(12) United States Patent
Lee et al.

(10) Patent No.: US 10,131,723 B2
(45) Date of Patent: Nov. 20, 2018

(54) LIGAND COMPOUND, CATALYST SYSTEM FOR OLEFIN OLIGOMERIZATION, AND METHOD FOR OLIGOMERIZING OLEFINS USING THE SAME

(71) Applicant: LG CHEM, LTD., Seoul (KR)

(72) Inventors: Yong Ho Lee, Daejeon (KR); Seul Ki Im, Daejeon (KR); Eun Ji Shin, Daejeon (KR); Ki Soo Lee, Daejeon (KR); Jin Young Park, Daejeon (KR); Seok Pil Sa, Daejeon (KR); Yoon Ki Hong, Daejeon (KR)

(73) Assignee: LG Chem, Ltd., Seoul (KR)

( * ) Notice: Subject to any disclaimer, the term of this patent is extended or adjusted under 35 U.S.C. 154(b) by 0 days.

(21) Appl. No.: 15/528,686

(22) PCT Filed: Sep. 1, 2016

(86) PCT No.: PCT/KR2016/009794
§ 371 (c)(1),
(2) Date: May 22, 2017

(87) PCT Pub. No.: WO2017/039353
PCT Pub. Date: Mar. 9, 2017

(65) Prior Publication Data
US 2017/0260305 A1    Sep. 14, 2017

(30) Foreign Application Priority Data
Sep. 2, 2015    (KR) .......... 10-2015-0124380

(51) Int. Cl.
| | | |
|---|---|---|
| *C07C 11/02* | (2006.01) | |
| *B01J 31/34* | (2006.01) | |
| *C08F 110/02* | (2006.01) | |
| *C08F 4/602* | (2006.01) | |
| *C08F 4/69* | (2006.01) | |
| *C08F 4/70* | (2006.01) | |
| *C08F 10/00* | (2006.01) | |
| *C08F 10/02* | (2006.01) | |
| *C07F 9/50* | (2006.01) | |
| *B01J 31/14* | (2006.01) | |
| *C07C 2/36* | (2006.01) | |
| *B01J 31/18* | (2006.01) | |

(52) U.S. Cl.
CPC ............ *C08F 110/02* (2013.01); *B01J 31/14* (2013.01); *C07C 2/36* (2013.01); *C07F 9/5027* (2013.01); *C08F 4/602* (2013.01); *C08F 4/69* (2013.01); *C08F 4/70* (2013.01); *C08F 10/00* (2013.01); *C08F 10/02* (2013.01); *B01J 31/189* (2013.01); *B01J 31/34* (2013.01); *C07C 2531/14* (2013.01); *C07C 2531/24* (2013.01)

(58) Field of Classification Search
CPC ........ C07F 11/00; C07F 11/005; B01J 31/189
See application file for complete search history.

(56) References Cited

U.S. PATENT DOCUMENTS

| | | | |
|---|---|---|---|
| 5,750,817 A | 5/1998 | Tanaka et al. | |
| 5,756,417 A | 5/1998 | De Boer et al. | |
| 6,555,633 B1 | 4/2003 | Tanaka et al. | |
| 6,787,499 B2 | 9/2004 | Tanaka et al. | |
| 6,803,431 B1 | 10/2004 | Mihan et al. | |
| 6,844,290 B1 | 1/2005 | Maas et al. | |
| 6,887,958 B1 | 5/2005 | Mihan et al. | |
| 7,378,537 B2 | 5/2008 | Small et al. | |
| 7,910,670 B2 | 3/2011 | Knudsen et al. | |
| 7,964,763 B2 * | 6/2011 | Dixon ............... | B01J 31/18 585/350 |
| 8,334,420 B2 | 12/2012 | Small et al. | |
| 2008/0207857 A1 | 8/2008 | Small et al. | |
| 2011/0282016 A1 * | 11/2011 | Carter ............... | C07C 2/36 526/145 |
| 2012/0172645 A1 | 7/2012 | Sydora | |
| 2015/0152200 A1 | 6/2015 | Hanton et al. | |
| 2016/0045906 A1 | 2/2016 | Sa et al. | |
| 2016/0122371 A1 | 5/2016 | Lee et al. | |
| 2016/0207946 A1 | 7/2016 | Shin et al. | |

FOREIGN PATENT DOCUMENTS

| | | | | |
|---|---|---|---|---|
| CN | 1651142 A | 8/2005 | | |
| CN | 104511311 A | 4/2015 | | |
| KR | 1994-0019666 A | 9/1994 | | |
| KR | 1996-7003945 A | 8/1996 | | |
| KR | 10-2001-0089115 | 9/2001 | | |
| KR | 10-2001-0108427 A | 12/2001 | | |
| KR | 10-2013-0142151 A | 12/2013 | | |
| KR | 10-2015-0006474 A | 1/2015 | | |
| KR | 10-2015-0057988 A | 5/2015 | | |
| WO | 2004/056477 A1 | 7/2004 | | |
| WO | 2004/056479 A1 | 7/2004 | | |
| WO | WO 2004/056477 A1 * | 7/2004 | .............. | B01J 31/18 |
| WO | WO 2004/056479 A1 * | 7/2004 | .............. | B01J 31/18 |

OTHER PUBLICATIONS

"High Activity Ethylene Trimerisation Catalysts Based on Diphosphine Ligands"; Carter, et al.; Chem. Commun., 2002, 858-859.
Blann, et al.: "Ethylene tetramerisation: Subtle effects exhibited by N-substituted diphosphinoamine ligands", KP022142429, Elsevier, Journal of Catalysis, vol. 249, No. 2, Jul. 4, 2007, pp. 244-249.

* cited by examiner

*Primary Examiner* — Rip A Lee
(74) *Attorney, Agent, or Firm* — Dentons US LLP

(57) ABSTRACT

The present invention relates to a compound represented by the chemical formula 1, a catalyst system for olefin oligomerization comprising the same, and a method for oligomerizign olefins using the same, and the catalyst system for olefin oligomerization according to the present invention has excellent catalytic activity as well as high selectivity for 1-hexene or 1-octene, thereby enabling more efficient preparation of alpha-olefins.

11 Claims, No Drawings

LIGAND COMPOUND, CATALYST SYSTEM FOR OLEFIN OLIGOMERIZATION, AND METHOD FOR OLIGOMERIZING OLEFINS USING THE SAME

CROSS-REFERENCE TO RELATED APPLICATION(S)

This application is a National Stage Entry of International Application No. PCT/KR2016/009794, filed on Sep. 1, 2016, and claims the benefit of and priority to Korean Application No.10-2015-0124380, filed on Sep. 2, 2015, all of which are hereby incorporated by reference in their entirety for all purposes as if fully set forth herein.

TECHNICAL FIELD

The present invention relates to a ligand compound, a catalyst system for olefin oligomerization, and a method for oligomerizing olefins using the same.

BACKGROUND OF ART

Linear alpha-olefins are widely used commercially as important materials used for comonomers, detergents, lubricants, plasticizers, etc., and in particular, 1-hexene and 1-octene are widely used as comonomers for controlling the density of polyethylene during the preparation of linear low-density polyethylene (LLDPE).

In existing preparation processes of linear low-density polyethylene (LLDPE), in order to control the density by forming branches in a polymer backbone, ethylene is copolymerized with alpha-olefins, for example, 1-hexene and 1-octene, as comonomers.

Accordingly, for the preparation of LLDPPE with a high content of copolymers, there was a problem in that the cost of comonomers occupies a large part of preparation costs. There have been various attempts to solve these problems.

In addition, since alpha-olefins have various different application fields or market sizes according to the kind, a technology of selectively producing a specific olefin is commercially very important, and recently, many studies are being progressed on the chromium catalyst technology for preparing 1-hexene or 1-octene with high selectivity through selective ethylene oligomerization.

Existing commercial preparation methods for preparing 1-hexene or 1-octene include the SHOP process of Shell Chemical, the Ziegler process of Chevron Philips, and the like, whereby C4-C20 alpha-olefins with a wide distribution can be produced.

As a catalyst for trimerization of ethylene, a chromium-based catalyst using a ligand of the general formula (R1)(R2)X—Y—X(R3)(R4) has been proposed. In the formula above, X is phosphorus, arsenic, or antimony, Y is a linking group such as —N(R5)-, and at least one of R1, R2, R3, and R4 has a polar or electron-donating substituent.

Additionally, as a ligand that exhibits catalytic activity to 1-hexene under catalytic conditions, studies have been progressed on o-ethylphenyl)$_2$PN(Me)P(o-ethylphenyl)$_2$, which does not have a polar substituent on at least one of R1, R2, R3 and R4 (*Chem. Commun.*, 2002, 858).

However, with regard to ligands containing heteroatoms of the above-mentioned prior art, there has been a continuing demand for multimerization reaction activity arid high selectivity which are consistently maintained during the reaction when preparing 1-octene or 1-hexene.

DETAILED DESCRIPTION OF THE INVENTION

Technical Problem

It is an object of the present invention to provide a novel ligand compound that can oligomerize olefins with high catalytic activity and selectivity, a catalyst system for olefin oligomerization including the same, and a method for oligornerizing olefins using the same.

Technical Solution

In order to achieve the objects, the present invention provides a compound represented by the chemical formula 1:

[Chemical Formula 1]

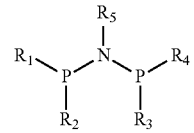

in Chemical Formula 1, $R_1$ to $R_4$ are each independently $C_{6-20}$ aryl unsubstituted or substituted with $C_{1-20}$ alkyl, and $R_5$ is $C_{6-20}$ aryl substituted with a vinyl group, or $C_{1-20}$ alkyl substituted with a vinyl group.

The present invention relates to a ligand compound constituting a catalyst system for olefin oligomerization together with a source of transitional metal and a cocatalyst. The compound represented by the chemical formula 1 is a P—N—P type ligand compound, and phosphorus and nitrogen are substituted with $C_{6-20}$ aryl or $C_{1-20}$ alkyl to give a steric bulk, thereby enabling selective olefin oligomerization.

In addition, $R_5$ is substituted with a vinyl group, and although not theoretically limited, the vinyl group is a terminal alkene, which induces oligomerization between the ligand compounds during olefin oligomerization to produce a multinuclear catalyst or reacts directly or indirectly with olefins to enable selective olefin oligomerization.

Preferably, the $R_1$ to $R_4$ are each independently phenyl or naphthyl.

Further, preferably, the $R_1$ to $R_4$ are identical to one another.

Further, preferably, the $R_1$ to $R_4$ are phenyl.

In addition, the $R_5$ is preferably phenyl substituted with a vinyl group, and more preferably 4-vinylphenyl.

In addition, preferably, only one of the $R_1$ to $R_5$ is substituted with a vinyl group.

A representative example of the compound represented by the chemical formula 1 is as follows:

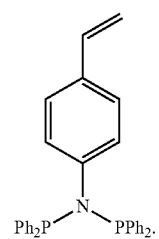

In addition, the compound represented by the chemical formula 1 above includes all possible optical isomers.

Further, the present invention provides a method for preparing the compound represented by the chemical formula 1 above, as shown in the following Reaction Scheme 1:

[Reaction Scheme 1]

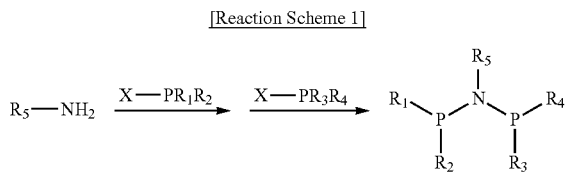

In Reaction Scheme 1, the definitions of $R_1$ to $R_5$ are the same as defined above, and each of X is independently halogen, and preferably chloro.

In Reaction Scheme 1, the order of the first step and the second step may be changed, and if $X\text{—}PR_1R_2$ and $X\text{—}PR_3R_4$ are identical, the second step may be omitted. As the solvent for the reaction, dichloromethane is preferable, and the reaction is carried out preferably in the presence of triethylamine.

Additionally, the present invention provides a catalyst system for olefin oligomerization, comprising the compound represented by the chemical formula 1, a source of transition metal, and a cocatalyst.

As used herein, the term "olefin oligomerization" means polymerization of a small number of olefins. Depending on the number of olefins to be polymerized, it is referred to as trimerization or tetramerization, and is collectively referred to as multimerization. In particular, in the present invention, it refers to selectively preparing 1-hexene and 1-octene, which are the main comonomers of LLDPE, from ethylene.

Such a selective olefin oligomerization reaction is closely related to a catalyst system used. A catalyst system used in olefin oligomerization reactions comprises a source of transition metal functioning as a main catalyst, and a cocatalyst, wherein the structure of an active catalyst can be modified according to the chemical structure of a ligand, thereby varying olefin selectivity.

As described above, the compound represented by the chemical formula 1 acts as a ligand in the catalyst system for olefin oligomerization, and enables selective olefin oligomerization due to steric hindrance and the presence of a vinyl group.

The source of transition metal of the catalyst system for olefin oligomerization of one embodiment described above functions as a main catalyst and may preferably be at least one selected from the group consisting of chromium(III) acetylacetonate, chromium trichloride tris-tetrahydrofuran, chromium(III)-2-ethylhexanoate, chromium(III)tris(2,2,6,6-tetramethyl-3,5-heptanedionate), chromium(III)benzoylacetonate, chromium (III)hexafluoro-2,4-pentanedionate, and chromium (III) acetate hydroxide.

Further, the cocatalyst is an organometallic compound comprising a Group 13 metal, and is not particularly limited, as long as it can be generally used when multimerizing olefins in the presence of a catalyst of a transition metal compound. Specifically, as the cocatalyst, at least one selected from the group consisting of compounds represented by Chemical Formulas 2 to 4 below can be used:

—[Al(R_6)—O]_c—   [Chemical Formula 2]

in Chemical Formula 2,
$R_6$ is each independently halogen, $C_{1-20}$ alkyl, or $C_{1-20}$ haloalkyl, and
c is an integer of 2 or greater, D(R_7)_3   [Chemical Formula 3]

in Chemical Formula 3,
D is aluminum or boron, and
$R_7$ is each independently hydrogen, halogen, $C_{1-20}$ hydrocarbyl, or $C_{1-20}$ hydrocarbyl substituted with halogen,

[L-H]^+[Q(E)_4]^−   [Chemical Formula 4]

in Chemical Formula 4,
L is a neutral Lewis base,
[L-H]^+ is a Brønsted acid,
Q is $B^{3+}$ or $Al^{3+}$,
E is each independently $C_{6-20}$ aryl or $C_{1-20}$ alkyl, wherein the $C_{6-20}$ aryl or $C_{1-20}$ alkyl is unsubstituted or substituted with at least one substituent selected from the group consisting of halogen, $C_{1-20}$ alkyl, $C_{1-20}$ alkoxy, and phenoxy.

The compound represented by the chemical formula 2 may be, for example, modified methyl aluminoxane (MMAO), methyl aluminoxane (MAO), ethyl aluminoxane, isobutyl aluminoxane, butyl aluminoxane, etc.

The alkyl metal compound represented by the chemical formula 3 may be, for example, trimethylaluminum, triethylaluminum, triisobutylaluminum, tripropylaluminum, tributylaluminum, dimethylchloroaluminum, dimethylisobutylaluminum, dimethylethylaluminum, diethylchloroaluminum, triisopropylaluminum, tri-s-butylaluminum, tricyclopentylaluminum, tripentylaluminum, triisopentylaluminum, trihexylaluminum, ethyldimethylaluminum, methyldiethylaluminum, triphenylaluminum, tri-p-tolylaluminum, dimethylaluminum methoxide, dimethylaluminum ethoxide, trimethylboron, triethylboron, triisobutylboron, tripropylboron, tributylboron, etc.

The compound represented by the chemical formula 4 may be, for example, triethylammonium tetraphenylboron, tributylammonium tetraphenylboron, trimethylammonium tetraphenylboron, tripropylammonium tetraphenylboron, trimethylammonium tetra(p-tolyl)boron, tripropylammonium tetra(p-tolyl) boron, triethylammonium tetra(o,p-dimethylphenyl) boron, trimethylammonium tetra(o,p-dimethylphenyl)boron, tributylammonium tetra(p-trifluoromethylphenyl)boron, trimethylammonium tetra(p-trifluoromethylphenyl)boron, tributylammonium tetrapentafluorophenylboron, N,N-diethylanilinium tetraphenylboron, N,N-diethylanilinium tetraphenylboron, N,N-diethylanilinium tetrapentafluorophenylboron, diethylammonium tetrapentafluorophenylboron, triphenylphosphonium tetraphenylboron, trimethylphosphonium tetraphenylboron, triethylammonium tetraphenylaluminum, tributylammonium tetraphenylaluminum, trimethylammonium tetraphenylaluminum, tripropylammonium tetraphenylaluminum, trimethylammonium tetra(p-tolyl) aluminum, tripropylammonium tetra(p-tolyl)aluminum, triethylammonium tetra(o,p-dimethylphenyl)aluminum, tributylammonium tetra(p-trifluoromethylphenyl)aluminum, trimethylammonium tetra(p-trifluoromethylphenyl)aluminum, tributylammonium tetrapentafluorophenylaluminum, N,N-diethylanilinium tetraphenylaluminum, N,N-diethylanilinium tetraphenylaluminum, N,N-diethylanilinium tetrapentafluorophenylaluminum, diethylammonium tetrapentafluorophenylaluminum, triphenylphosphonium tetraphenylaluminum, trimethylphosphonium tetraphenylaluminum, triphenylcarbonium tetraphenylboron, triphenylcarbonium tetraphenylaluminum, triphenylcarbonium tetra (p-trifluoromethylphenyl)boron, triphenylcarbonium tetrapentafluorophenylboron, etc.

As the cocatalyst of the catalyst system for olefin oligomerization of one embodiment, aluminoxane may preferably be used, and more preferably, methyl aluminoxane (MAO) or modified methyl aluminoxane (MMAO) may be used.

The catalyst system for olefin oligomerization may have a molar ratio of the compound represented by the chemical formula 1: a source of transition metal : a cocatalyst at a molar ratio of about 0.5:1:1 to about 10:1:10,000, preferably about 0.5:1:100 to about 5:1:3,000, so as to increase selectivity to linear alpha-olefin and multimerization activity. However, the present invention is not limited thereto.

In the catalyst system comprising the compound represented by the chemical formula 1, a source of transition metal, and a cocatalyst, the three components of the catalyst system can be added simultaneously or sequentially in a random order in any suitable solvent in the presence or absence of monomers, and be obtained as a catalyst having activity. Suitable solvents include heptane, toluene, cyclohexane, methylcyclohexane, 1-hexene, diethyl ether, tetrahydrofuram, acetonitrile, dichloromethane, chloroform, chlorobenzene, methanol, acetone, etc., but are not limited thereto.

Meanwhile, according to another embodiment of the present invention, a method for preparing an olefin oligomer, comprising multimimerizing olefins in the presence of the catalyst system for olefin oligomerization, may be provided. If the catalyst system for olefin oligomerization according to the present invention is used, a method for olefin oligomerization with improved activity and selectivity may be provided. In this case, olefin is preferably ethylene.

The olefin oligomerization according to the present invention may be conducted as a homogeneous liquid phase reaction, a slurry reaction wherein a catalyst system is not dissolved in part or in whole, a two-phase liquid/liquid reaction, or a bulk phase reaction or a gas phase reaction wherein a product olefin acts as a main medium, in the absence or presence of an inert solvent, using the catalyst system for olefin oligomerization arid a common device and contact technology, and the homogeneous liquid phase reaction is preferable.

The olefin oligomerization reaction can be carried out in any inert solvent that does not react with a catalyst compound and an activator. Suitable inert solvents include benzene, toluene, xylene, cumene, heptane, cyclohexane, methylcyclohexane, methylcyclopentane, hexane, pentane, butane, isobutane, etc., but are not limited thereto. In this case, the solvent can be used by treating with a small amount of alkylaluminum and thereby removing a small amount of water or air acting as a catalyst poison.

The olefin oligomerization reaction may be carried out at a temperature of about 5° C. to about 200° C., preferably of about 30° C. to about 150° C. Further, the olefin oligomerization reaction may be carried out at a pressure from about 1 bar to about 300 bar, preferably at a pressure from about 2 bar to about 150 bar.

According to one embodiment of the present invention, it was confirmed that as a result of oligomerizing ethylene with a catalyst system using the compound represented by chemical formula 1 as a ligand, 1-hexene and 1-octene are selectively synthesized.

Advantageous Effects

A catalyst system comprising the compound according to the present invention can oligomerize ethylene with higher catalytic activity and selectivity than existing catalyst systems.

DETAILED DESCRIPTION OF THE EMBODIMENTS

Hereinafter, preferred examples are presented to aid in understanding of the present invention. However, these examples are only for illustrative purposes, and the scope of the present invention is not limited thereto.

In the preparation of the following ligand compounds, all reactions proceeded using the Schlenk technique or glove box under an argon atmosphere. The synthesized ligands were analyzed by obtaining $^1$H (500 MHz) and $^{31}$P (202 MHz) NMR spectra using a Varian 500 MHz spectrometer. Shift was expressed as ppm downfield from TMS with a residual solvent peak as a reference. A phosphorous probe was calibrated with aqueous $H_3PO_4$.

EXAMPLE

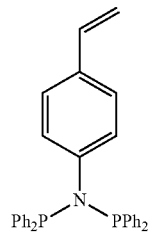

Under argon, 4-vinylaniline (10 mmol) and triethylamine (30 mmol) were dissolved in dichloromethane (80 mL). While the flask was immersed in a water bath, chlorodiphenylphosphine (20 mmol) was slowly added thereto, and the mixture was stirred overnight. The solvent was removed under vacuum, THF was added, and the mixture was stirred sufficiently to remove a triethylammnoium chloride salt with an air-free glass filter. The solvent was removed from the filtrate to obtain the desired compound.

$^{31}$P NMR (500 MHz, CDCl$_3$): 68.658 (s)

Comparative Example

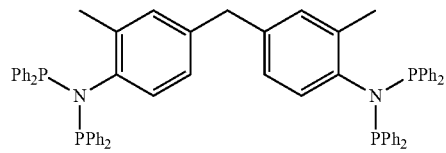

Under argon, 4-4'-methylenebis(2-methylaniline) (10 mmol) and triethylamine (30 mmol) were dissolved in dichloromethane (80 mL). While the flask was immersed in a water bath, chlorophenylphosphine (20 mmol) was slowly added thereto, and the mixture was stirred overnight. The solvent was removed under vacuum, MTBE was added thereto, and the mixture was stirred sufficiently to remove a triethylammonium chloride salt with an air-free glass filter. The solvent was removed from the filtrate to obtain the desired compound.

$^{31}$ NMR (500 MHz, CDCl$_3$): 61.7 (s)

Experimental Example (Step 1)
Under an argon gas, Cr(acac)$_3$ (17.5 mg, 0.05 mmol) and the compound prepared in the Example above (0.055 mmol) were added to a flask, and 100 mL of methylcyclohexane was added, and the mixture was stirred to prepare a 0.5 mM solution.

(Step 2)
A Parr reactor with a capacity of 600 mL was prepared and vacuumed at 120° C. for 2 hours, then the temperature was lowered to 60° C., and the inside was replaced with argon. Thereafter, 120 g of methylcyclohexane was injected into the Parr reactor, and then 20 g of methylcyclohexane, 1.6 mL of MMAO (8.6 wt % iso-heptane solution, Ar/Cr=1200), and 5 mL (2.5 μmol) of the 0.5 mM solution prepared in the step 1 were injected into a 50 mL flask which was separately dried and replaced with argon, and the mixture was stirred for 1 minute. The solution in the flask was transferred to the Parr reactor using a cannula.

A valve of an ethylene line adjusted to 60 bar was opened to fill the inside of the reactor with ethylene, and then adjusted to preheat to 45° C., and the mixture was stirred at 1000 rpm for 15 minutes. The ethylene line valve was closed, the reactor was cooled to 0° C. with a dry ice/acetone bath, non-reacted ethylene was slowly vented, and then 1 mL of nonane (GC internal standard) was added. After stirring for 10 seconds, 2 mL of the liquid portion of the reactor was taken and quenched with water, and the organic layer was filtered with a PTFE syringer filter to perform GC analysis.

(Step 3)
400 mL of ethanol/HCl (10 vol %) was added to the remaining reaction mixture, and the mixture was stirred and filtered to obtain a polymer. The obtained polymer was dried in a vacuum oven at 60° C. overnight.

Comparative Experimental Example

The experiment was carried out in the same manner as in the Experimental Example, except that the compound prepared in the Comparative Example was used instead of the compound prepared in the Example.

The results of the above Experimental Example and Comparative Experimental Example are shown in Table 1 below.

TABLE 1

| Ligand | Activity ton/molCr/hr | 1-C6 wt % | 1-C8 wt % | C10-C40 wt % | HAO[1] wt % | Solid[2] wt % | iso-C6s wt % | iso-C8 wt % |
|---|---|---|---|---|---|---|---|---|
| Example | 143 | 19.3 | 62.2 | 9.0 | 81.5 | 0.4 | 6.7 | 1.1 |
| Comparative Example | 62 | 16.7 | 60.9 | 8.8 | 77.6 | 0.9 | 9.5 | 1.6 |

[1]HAO: Sum of 1-C6 and 1-C8 (high alpha-olefin)
[2]Solid: Solid alpha-olefin

As shown in Table 1 above, when the compound of the Example according to the present invention was used as a ligand, it was confirmed that the catalytic activity and the selectivity for 1-hexene and 1-octene were higher compared with those of the Comparative Example.

The invention claimed is:

1. A compound represented by the following Chemical Formula 1:

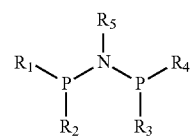

[Chemical Formula 1]

in Chemical Formula 1,
R$_1$ to R$_4$ are each independently C$_{6-20}$ aryl unsubstituted or substituted with C$_{1-20}$ alkyl, and
R$_5$ is C$_{6-20}$ aryl substituted with a vinyl group.

2. The compound of claim 1, wherein R$_1$ to R$_4$ are each independently phenyl or naphthyl.

3. The compound of claim 1, wherein R$_1$ to R$_4$ are identical to one another.

4. The compound claim 3, wherein R$_1$ to R$_4$ are phenyl.

5. The compound of claim 1, wherein R$_5$ is phenyl substituted with a vinyl group.

6. The compound of claim 5, wherein R$_5$ is 4-vinylphenyl.

7. The compound of claim 1, wherein the compound is

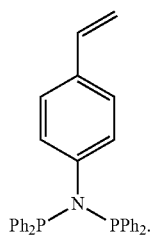

8. A catalyst system for olefin oligomerization, comprising: the compound according to claim 1; a source of transition metal; and a cocatalyst.

9. The catalyst system for olefin oligomerization of claim 8, wherein the source of transition metal is at least one selected from the group consisting of chromium(III) acetylacetonate, chromium trichloride tris-tetrahydrofuran, chromium(III-2-ethylhexanoate, chromium(III) tris-(2,2,6,6-tetramethyl-3,5-heptanedionate), chromium(III)benzoylacetonate, chromium (III) hexafluoro-2,4-pentanedionate, and chromium(III)acetate hydroxide.

10. The catalyst system of claim 8,
wherein the cocatalyst is at least one selected from the group consisting of the compounds represented by the following Chemical Formulas 2 to 4:

$$—[Al(R_6)—O]_c—$$ [Chemical Formula 2]

in Chemical Formula 2,
$R_6$ is each independently halogen, $C_{1-20}$ alkyl, or $C_{1-20}$ haloalkyl, and
C is an integer of 2 or greater, $$D(R_7)_3$$ [Chemical Formula 3]

in Chemical Formula 3,
D is aluminum or boron, and
$R_7$ is each independently hydrogen, halogen, $C_{1-20}$ hydrocarbyl, or $C_{1-20}$ hydrocarbyl substituted with halogen, $$[L-H]^+[Q(E)_4]^-$$ [Chemical Formula 4]

in Chemical Formula 4,
L is a neutral Lewis base,
$[L-H]^+$ is a Brønsted acid,
Q is $B^{3+}$ or $Al^{3+}$, and
E is each independently $C_{6-20}$ aryl or $C_{1-20}$ alkyl, wherein the $C_{6-20}$ aryl or $C_{1-20}$ alkyl is unsubstituted or substituted with at least one substituent selected from the group consisting of halogen, $C_{1-20}$ alkyl, $C_{1-20}$ alkoxy, and phenoxy.

11. A method for olefin oligomerization, comprising multimenzmg olefins in the presence of the catalyst system for olefin oligomerization of claim 8.

* * * * *